United States Patent [19]

Murahashi et al.

[11] Patent Number: 5,426,237
[45] Date of Patent: Jun. 20, 1995

[54] PROCESS FOR PRODUCING ALCOHOLS AND KETONES

[75] Inventors: Shun-Ichi Murahashi, Ikeda; Yoshiaki Oda, Toyonaka, both of Japan

[73] Assignee: Sumitomo Chemical Co., Ltd., Osaka, Japan

[21] Appl. No.: 217,218

[22] Filed: Mar. 24, 1994

Related U.S. Application Data

[63] Continuation of Ser. No. 924,931, Aug. 5, 1992, abandoned.

[30] Foreign Application Priority Data

Aug. 8, 1991 [JP] Japan .................. 3-199221
Oct. 23, 1991 [JP] Japan .................. 3-275381
Oct. 24, 1991 [JP] Japan .................. 3-277689
Mar. 11, 1992 [JP] Japan .................. 4-052439

[51] Int. Cl.$^6$ .................................. C07C 45/33
[52] U.S. Cl. .................... 568/360; 568/320; 568/321; 568/399; 568/815; 568/836; 568/910
[58] Field of Search ............. 568/320, 321, 399, 815, 568/836, 910

[56] References Cited

U.S. PATENT DOCUMENTS

| | | | |
|---|---|---|---|
| 3,025,306 | 3/1962 | Guest et al. | 568/399 |
| 3,483,222 | 12/1969 | Sennewald et al. | 568/379 |
| 3,931,330 | 1/1976 | Aprahamian | 568/360 |
| 4,341,907 | 7/1982 | Zelonka | 568/360 |

FOREIGN PATENT DOCUMENTS

| | | | |
|---|---|---|---|
| 0126488 | 5/1984 | European Pat. Off. | 568/360 |
| 126488 | 11/1984 | European Pat. Off. | 568/399 |
| 1568214 | 12/1966 | Germany | 568/360 |
| 46-12456 | 3/1971 | Japan | 568/399 |
| 56-14095 | 4/1981 | Japan | 568/399 |
| 59-231077 | 12/1984 | Japan | 568/399 |
| 1197930 | 7/1970 | United Kingdom | 568/360 |
| 1206431 | 9/1970 | United Kingdom | 568/360 |

OTHER PUBLICATIONS

Galimor et al, Chem. Abst., vol. 108, #5421w (1988).

Murahashi et al, J.A.C.S., vol. 114, pp. 7913–7914 (1992).

(List continued on next page.)

*Primary Examiner*—James H. Reamer
*Attorney, Agent, or Firm*—Cushman Darby & Cushman

[57] ABSTRACT

The present invention provides a process for the oxidation of straight-chain, branched-chain or cyclic alkanes of 1–20 carbon atoms and benzene derivatives represented by the following formulas (1)–(2). The alcohols and ketones obtained by the oxidation of the alkanes mentioned above and those by the oxidation of the benzene derivatives mentioned above represented by the following formulas (3)–(6) are important as basic starting materials in producing various chemical products including resins, such as nylon and polyester, pharmaceuticals, agricultural chemicals, perfumes, dyes, etc.

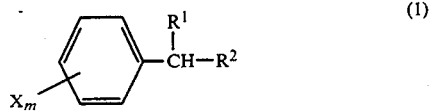

(1)

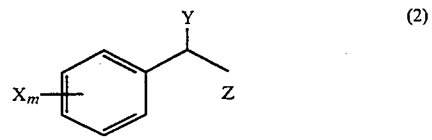

(2)

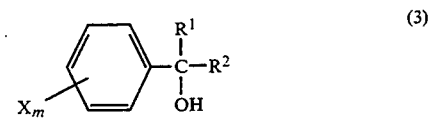

(3)

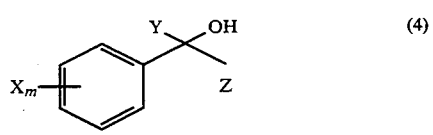

(4)

17 Claims, No Drawings

OTHER PUBLICATIONS

Swern, et al; "Epoxidation of Oleic Acid, Methyl Oleate & Oleyl Alcohol with Perbenzoic Acid"; Am.-Chem.Soc. (1944) vol. 66, 1925–27.

Swern, et al; "Chemistry of Epoxy Compounds.XII.1 Co-oxidation of Aldehydes and Oleic Acid, Methyl Oleate or Oleyl Alcohol", JACS, vol. 72, 4315–67, (1950).

Knopf, et al; "Oxirane durch Cooxidation von Alkenen und Aldehyden mit Sauerstoff" Synthesis (1944) 711–3.

Tsuchiya, et al.; "Liquid-phase Oxidation of 2-butene in the presence of Benzaldehyde" Canadian Journal of Chemistry, vol. 47, (1969) 3191–7.

Haber, et al; "Reactivity-Structure Correlations in Oxidation with Metalloporphyrins" Journal of Molecular Catalysis, vol. 52 (1989) 85–97.

Rogers et al.; "Iron Porphyrin catalysed Oxidation of Propanal and Cyclohexene by Molecular Oxygen" J. Chem. So., Chem. Commun, (1990) 1323–4.

Yamada et al; "Direct Epoxidation of Olefins Catalyzed by Nickel (II) Complexes with Molecular Oxygen and Aldehydes" Bull. Chem Soc. Jpn. (1991) vol. 64, 2109–2117.

Takai et al; "Aerobic Epoxidation of Olefinic Compounds Catalyzed by Tris (1,3-diketonato(iron(III)" Bull. Chem Soc Jap. (1991) vol. 64, 2513–8.

Kaneda et al; "Ruthenium-catalysed Oxidative Cleavage Reaction of Carbon-Carbon Double Bonds Using Molecular Oxygen" J.Chem. Soc., Chem. Commun., (1990) 1467–8.

Takai et al; "Aerobic Oxygenation of Olefinic Compounds into the Corresponding α-Hydroxy Ketones Using the Catalyst System of $OsO_4$ and Ni(II)Complex" Chemistry Letters, (1991) 1499–1502.

Yamada et al; "The Baeyer-Villiger Oxidation of Ketones Catalyzed by Nickel(II)Complexes with Combined Use of Molecular Oxygen and an Aldehyde" Chemistry Letters (1991) 641–4.

S. A. Miller; "Cyclohexane, Cyclohenanol and Cyclohexanone", Chemical and Process Engineering, Jun. 1969, 50(6), 63–72.

Barton et al; "Functionalization of Saturated Hydrocarbons, Part 4, 1, The Gif System for Selective Oxidation using Molecular Oxygen" J.Chem. Soc.Perkin Trans I (1986) 947–955.

PROCESS FOR PRODUCING ALCOHOLS AND KETONES

This is a continuation of application Ser. No. 07/924,931, filed on Aug. 5, 1992, which was abandoned upon the filing hereof.

BACKGROUND OF THE INVENTION

1. Field of the Invention

The present invention relates to a process for the oxidation of straight-chain, branched-chain or cyclic alkanes of 1-20 carbon atoms and benzene derivatives. The alcohols and ketones obtained by the oxidation of these alkanes and benzene derivatives are compounds which are important as basic starting materials in the production of various chemical products, including resins, such as nylon and polyesters, pharmaceuticals, agricultural chemicals, perfumes, dyes, etc.

2. Related Prior Art

For effective utilization of alkanes and benzene derivatives which occur naturally in abundance, the development of an efficient process for producing alcohols and ketones by direct oxidation of these alkanes and benzene derivatives is eagerly awaited.

However, unactivated alkanes, which have no active functional group, can be oxidized very difficultly. Although many researches have been reported on this subject, their results are not yet fully satisfactory for reasons of, for example, severe reaction conditions [Chem. Process Eng. (London), 1969, 50(6), 63] and complicated post-treatment steps required (J. Chem. Soc., Perkin Trans. I, 1986, 947).

SUMMARY OF THE INVENTION

The object of the present invention is to provide a process for producing alcohols and ketones advantageously by the oxidation of alkanes and benzene derivatives with oxygen using an easily available catalyst under mild conditions.

The present inventors have made extensive study to solve the above-mentioned problem and resultantly attained the present invention. Thus, according to the present invention, there is provided a process for producing the corresponding alcohols or ketones derived from alkanes defined below, or alcohols represented by the formula (3)

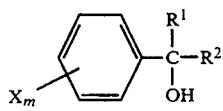

wherein $R^1$, $R^2$, X and m are as defined below, or by the formula (4)

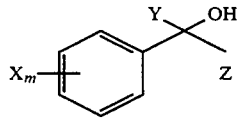

wherein X, Y, Z and m are as defined below, or ketones represented by the formula (5)

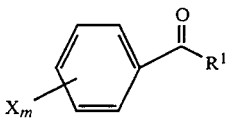

wherein $R^1$, X and m are as defined below, or by the formula (6)

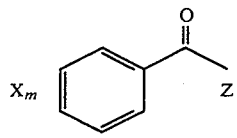

wherein X, Z and m are as defined below, which comprises reacting a straight-chain, branched-chain or cyclic alkane of 1-20 carbon atoms or a benzene derivative represented by the formula (1)

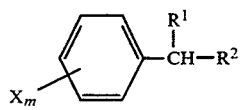

wherein $R^1$ and $R^2$ may be the same or different and each denote a hydrogen atom, $(C_1-C_{20})$alkyl group, alkyl group substituted with a halogen, alkoxy or phenoxy, phenyl group unsubstituted or substituted with a halogen, alkyl, alkoxy or phenoxy or phenylalkyl group unsubstituted or substituted with a halogen, alkyl, alkoxy or phenoxy, or they conjointly as $-CHR^1(R^2)$ in its entirety denote a $(C_3-C_{12})$cycloalkyl group unsubstituted or substituted with a halogen, alkyl, alkoxy, phenyl or phenoxy; X may be the same or different and denotes a hydrogen atom, halogen atom, $(C_1-C_6)$alkyl group, $(C_1-C_6)$alkoxy group, phenyl group or phenoxy group; and m denotes 1 or 2, or by the formula (2)

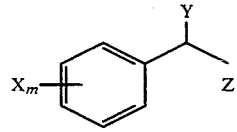

wherein Y denotes a hydrogen atom, halogen atom, $(C_1-C_6)$alkyl group, $(C_1-C_6)$alkoxy group, phenyl group or phenoxy group; Z denotes a group of $-CH_2CH_2-$, $-CH_2CH_2CH_2-$ or

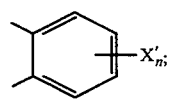

X and X' may be the same or different and each denote a hydrogen atom, halogen atom, $(C_1-C_6)$alkyl group, $(C_1-C_6)$alkoxy group, phenyl group or phenoxy group; and m and n each independently denote 1 or 2, with oxygen in the absence or presence of a proton source and in the presence of a transition metal catalyst and an aldehyde.

DETAILED DESCRIPTION OF THE INVENTION

The straight-chain, branched-chain or cyclic alkanes of 1–20 carbon atoms used as the starting material in the present invention may be, for example, methane, ethane, propane, n-butane, isobutane, n-pentane, n-hexane, n-heptane, n-octane, n-nonane, n-decane, n-undecane, n-dodecane, n-pentadecane, n-eicosane, 2-methylbutane, 2-methylheptane, 2-methyltetradecane, 2,6-dimethylheptane, 2,2,8-trimethylnonane, 3-methylpentane, 4-methylnonane, 4-n-propylnonane, 2,2-dimethylbutane, 2,2-dimethylpentane, 3,3-dimethylpentane, 2,2-dimethylhexane, 3,3-dimethylhexane, 3,3-dimethylnonane, 2,2-dimethyltridecane, 3,3-dimethyltridecane, 4,4-dimethylheptane, 4,4-dimethyldecane, 5,5-dimethylnonane, 5,5-dimethyltridecane, 7,7-dimethyltridecane, 2,2,8,8-tetramethylnonane, 4,4,5,5-tetramethyldecane, 5-ethyl-5-n-propyldecane, cyclopentane, cyclohexane, cycloheptane, cyclooctane, cyclododecane, methylcyclopentane, methylcyclohexane, ethylcyclohexane, ethylcyclooctane, 1,2-dimethylcyclohexane, decalin, norbornane, adamantane, etc.

The alcohols and ketones which are the objective compounds of the present invention can be obtained, by using the alkanes mentioned above, as the corresponding alcohols and ketones derived from the alkanes. Examples of the alcohols include methanol, ethanol, isopropyl alcohol, 2-butanol, tert-butanol, 2-pentanol, 3-pentanol, 2-hexanol, 3-hexanol, 2-heptanol, 3-heptanol, 4-heptanol, 2-octanol, 3-octanol, 4-octanol, 2-nonanol, 3-nonanol, 4-nonanol, 5-nonanol, 2-decanol, 3-decanol, 4-decanol, 5-decanol, 2-undecanol, 3-undecanol, 4-undecanol, 5-undecanol, 6-undecanol, 2-dodecanol, 3-dodecanol, 4-dodecanol, 5-dodecanol, 6-dodecanol, 2-pentadecanol, 3-pentadecanol, 4-pentadecanol, 5-pentadecanol, 6-pentadecanol, 7-pentadecanol, 8-pentadecanol, 2-eicosanol, 3-eicosanol, 4-eicosanol, 5-eicosanol, 6-eicosanol, 7-eicosanol, 8-eicosanol, 9-eicosanol, 10-eicosanol, 2-methyl-2-butanol, 3-methyl-2-butanol, 2-methyl-2-heptanol, 2-methyl-3-heptanol, 2-methyl-4-heptanol, 6-methyl-3-heptanol, 6-methyl-2-heptanol, 2-methyl-2-tetradecanol, 2-methyl-3-tetradecanol, 2-methyl-4-tetradecanol, 2-methyl-5-tetradecanol, 2-methyl-6-tetradecanol, 2-methyl-7-tetradecanol, 13-methyl-7-tetradecanol, 13-methyl-6-tetradecanol, 13-methyl-5-tetradecanol, 13-methyl-4-tetradecanol, 13-methyl-3-tetradecanol, 13-methyl-2-tetradecanol, 2,6-dimethyl-2-heptanol, 2,6-dimethyl-3-heptanol, 2,6-dimethyl-4-heptanol, 2,8,8-trimethyl-2-nonanol, 2,8,8-trimethyl-3-nonanol, 2,8,8-trimethyl-4-nonanol, 2,2,8-trimethyl-5-nonanol, 2,2,8-trimethyl-4-nonanol, 2,2,8-trimethyl-3-nonanol, 3-methyl-3-pentanol, 3-methyl-2-pentanol, 4-methyl-4-nonanol, 4-methyl-2-nonanol, 4-methyl-3-nonanol, 4-methyl-5-nonanol, 6-methyl-4-nonanol, 6-methyl-3-nonanol, 6-methyl-2-nonanol, 4-n-propyl-4-nonanol, 4-n-propyl-2-nonanol, 4-n-propyl-3-nonanol, 4-n-propyl-5-nonanol, 6-n-propyl-4-nonanol, 6-n-propyl-3-nonanol, 6-n-propyl-2-nonanol, 3,3-dimethyl-2-butanol, 2,2-dimethyl-3-pentanol, 4,4-dimethyl-2-pentanol, 3,3-dimethyl-2-pentanol, 2,2-dimethyl-3-hexanol, 5,5-dimethyl-3-hexanol, 5,5-dimethyl-2-hexanol, 3,3-dimethyl-2-hexanol, 4,4-dimethyl-3-hexanol, 4,4-dimethyl-2-hexanol, 3,3-dimethyl-2-nonanol, 3,3-dimethyl-4-nonanol, 3,3-dimethyl-5-nonanol, 7,7-dimethyl-4-nonanol, 7,7-dimethyl-3-nonanol, 7,7-dimethyl-2-nonanol, 2,2-dimethyl-3-tridecanol, 2,2-dimethyl-4-tridecanol, 2,2-dimethyl-5-tridecanol, 2,2-dimethyl-6-tridecanol, 2,2-dimethyl-7-tridecanol, 12,12-dimethyl-6-tridecanol, 12,12-dimethyl-5-tridecanol, 12,12-dimethyl-4-tridecanol, 12,12-dimethyl-3-tridecanol, 12,12-dimethyl-2-tridecanol, 3,3-dimethyl-2-tridecanol, 3,3-dimethyl-4-tridecanol, 3,3-dimethyl-5-tridecanol, 3,3-dimethyl-6-tridecanol, 3,3-dimethyl-7-tridecanol, 11,11-dimethyl-6-tridecanol, 11,11-dimethyl-5-tridecanol, 11,11-dimethyl-4-tridecanol, 11,11-dimethyl-3-tridecanol, 11,11-dimethyl-2-tridecanol, 4,4-dimethyl-2-heptanol, 4,4-dimethyl-3-heptanol, 4,4-dimethyl-2-decanol, 4,4-dimethyl-3-decanol, 4,4-dimethyl-5-decanol, 7,7-dimethyl-5-decanol, 7,7-dimethyl-4decanol, 7,7-dimethyl-3-decanol, 7,7-dimethyl-2-decanol, 5,5-dimethyl-2-nonanol, 5,5-dimethyl-3-nonanol, 5,5-dimethyl-4-nonanol, 5,5-dimethyl-2-tridecanol, 5,5-dimethyl-3-tridecanol, 5,5-dimethyl-4-tridecanol, 5,5-dimethyl-6-tridecanol, 5,5-dimethyl-7-tridecanol, 9,9-dimethyl-6-tridecanol, 9,9-dimethyl-5-tridecanol, 9,9-dimethyl-4-tridecanol, 9,9-dimethyl-3-tridecanol, 9,9-dimethyl-2-tridecanol, 7,7-dimethyl-2-tridecanol, 7,7-dimethyl-3-tridecanol, 7,7-dimethyl-4-tridecanol, 7,7-dimethyl-5-tridecanol, 7,7-dimethyl-6-tridecanol, 2,2,8,8-tetramethyl-3-nonanol, 2,2,8,8-tetramethyl-4-nonanol, 2,2,8,8-tetramethyl-5-nonanol, 4,4,5,5-tetramethyl-2-decanol, 4,4,5,5-tetramethyl-3-decanol, 6,6,7,7-tetramethyl-5-decanol, 6,6,7,7-tetramethyl-4-decanol, 6,6,7,7-tetramethyl-3-decanol, 6,6,7,7-tetramethyl-2-decanol, 5-ethyl-5-n-propyl-2-decanol, 5-ethyl-5-n-propyl-3-decanol, 5-ethyl-5-n-propyl-4-decanol, 6-ethyl-6-n-propyl-5-decanol, 6-ethyl-6-n-propyl-4-decanol, 6-ethyl-6-n-propyl-3-decanol, 6-ethyl-6-n-propyl-2-decanol, 3-n-butyl-3-n-propyl-2-octanol, 4-butyl-4-ethyl-2-nonanol, 4-butyl-4-ethyl-3-nonanol, cyclopentanol, cyclohexanol, cycloheptanol, cyclooctanol, cyclododecanol, 1-methylcyclopentanol, 2-methylcyclopentanol, 3-methylcyclopentanol, 1-methylcyclohexanol, 2-methylcyclohexanol, 3-methylcyclohexanol, 4-methylcyclohexanol, 1-ethylcyclohexanol, 2-ethylcyclohexanol, 3-ethylcyclohexanol, 4-ethylcyclohexanol, 1-cyclohexylethanol, 1-ethylcyclooctanol, 2-ethylcyclooctanol, 3-ethylcyclooctanol, 4-ethylcyclooctanol, 5-ethylcyclooctanol, 1-cyclooctylethanol, 1,2-dimethylcyclohexanol, 2,3-dimethylcyclohexanol, 3,4-dimethylcyclohexanol, 9-decalol, 1-decalol, 2-decalol, endo-norborneol, exonorborneol, 1-adamantanol, 2-adamantanol, etc. Examples of the ketones include acetone, 2-butanone, 2-pentanone, 3-pentanone, 2-hexanone, 3-hexanone, 2-heptanone, 3-heptanone, 4-heptanone, 2-octanone, 3-octanone, 4-octanone, 2-nonanone, 3-nonanone, 4-nonanone, 5-nonanone, 2-decanone, 3-decanone, 4-decanone, 5-decanone, 2-undecanone, 3-undecanone, 4-undecanone, 5-undecanone, 6-undecanone, 2-dodecanone, 3-dodecanone, 4-dodecanone, 5-dodecanone, 6-dodecanone, 2-pentadecanone, 3-pentadecanone, 4-pentadecanone, 5-pentadecanone, 6-pentadecanone, 7-pentadecanone, 8-pentadecanone, 2-eicosanone, 3-eicosanone, 4-eicosanone, 5-eicosanone, 6-eicosanone, 7-eicosanone, 8-eicosanone, 9-eicosanone, 10-eicosanone, 3-methyl-2-butanone, 2-methyl-3-heptanone, 2-methyl-4-heptanone, 6-methyl-3-heptanone, 6-methyl-2-heptanone, 2-methyl-3-tetradecanone, 2-methyl-4-tetradecanone, 2-methyl-5-tetradecanone, 2-methyl-6-tetradecanone, 2-methyl-7-tetradecanone, 13-methyl-7-tetradecanone, 13-methyl-6-tetradecanone, 13-methyl-5-tetradecanone, 13-methyl-4-tetradecanone, 13-methyl-3-tetradecanone, 13-methyl-2-tetradecanone, 2,6-dimethyl-3-heptanone, 2,6-dimethyl-4-heptanone, 2,8,8-trimethyl-3-nonanone, 2,8,8-trimethyl-4-nonanone, 2,2,8-trimethyl-5-nonanone, 2,2,8-trimethyl-4-nonanone, 2,2,8-trimethyl-3-nonanone, 3-methyl-2-pentanone, 4-methyl-2-nonanone, 4-methyl-3-nonanone, 4-methyl-5-nonanone, 6-methyl-4-nonanone, 6-methyl-3-nonanone, 6-methyl-2-nonanone, 4-n-propyl-2-nonanone, 4-n-propyl-3-nonanone, 4-n-propyl-5-nonanone, 6-n-propyl-4-nonanone, 6-n-propyl-3-nonanone, 6-n-propyl-2-nonanone, 3,3-dimethyl-2-butanone, 2,2-dimethyl-3-pentanone, 4,4-dimethyl-2-pentanone, 3,3-dimethyl-2-pentanone, 2,2-dimethyl-3-hexanone, 5,5-dimethyl-3-hexanone, 5,5-dimethyl-2-hexanone, 3,3-dimethyl-2-hexanone, 4,4-dimethyl-3-hexanone, 4,4-dimethyl-2-hexanone, 3,3-dimethyl-2-nonanone, 3,3-dimethyl-4-nonanone, 3,3-dimethyl-5-nonanone, 7,7-dimethyl-4-nonanone, 7,7-dimethyl-3-nonanone, 7,7-dimethyl-2-nonanone, 2,2-dimethyl-3-tridecanone, 2,2-dimethyl-4-tridecanone, 2,2-dimethyl-5-tridecanone, 2,2-dimethyl-6-tridecanone, 2,2-dimethyl-7-tridecanone, 12,12-dimethyl-6-tridecanone, 12,12-dimethyl-5-tridecanone, 12,12-dimethyl-4-tridecanone, 12,12-dimethyl-3-tridecanone, 12,12-dimethyl-2-tridecanone, 3,3-dimethyl-2-tridecanone, 3,3-dimethyl-4-tridecanone, 3,3-dimethyl-5-tridecanone, 3,3-dimethyl-6-tridecanone, 3,3-dimethyl-7-tridecanone, 11,11-dimethyl-6-tridecanone, 11,11-dimethyl-5-tridecanone, 11,11-dimethyl-4-tridecanone, 11,11-dimethyl-3-tridecanone, 11,11-dimethyl-2-tridecanone, 4,4-dimethyl-2-heptanone, 4,4-dimethyl-3-heptanone, 4,4-dimethyl-2-decanone, 4,4-dimethyl-3-decanone, 4,4-dimethyl-5-decanone, 7,7-dimethyl-5-decanone, 7,7-dimethyl-4-decanone, 7,7-dimethyl-3-decanone, 7,7-dimethyl-2-decanone, 5,5-dimethyl-2-nonanone, 5,5-dimethyl-3-nonanone, 5,5-dimethyl-4-nonanone, 5,5-dimethyl-2-tridecanone, 5,5-dimethyl-3-tridecanone, 5,5-dimethyl-4-tridecanone, 5,5-dimethyl-6-tridecanone, 5,5-dimethyl-7-tridecanone, 9,9-dimethyl-6-tridecanone, 9,9-dimethyl-5-tridecanone, 9,9-dimethyl-4-tridecanone, 9,9-dimethyl-3-tridecanone, 9,9-dimethyl-2-tridecanone, 7,7-dimethyl-2-tridecanone, 7,7-dimethyl-3-tridecanone, 7,7-dimethyl-4-tridecanone, 7,7-dimethyl-5-tridecanone, 7,7-dimethyl-6-tridecanone, 2,2,8,8-tetramethyl-3-nonanone, 2,2,8,8-tetramethyl-4-nonanone, 2,2,8,8-tetramethyl-5-nonanone, 4,4,5,5-tetramethyl-2-decanone, 4,4,5,5-tetramethyl-3-decanone, 6,6,7,7-tetramethyl-5-decanone, 6,6,7,7-tetramethyl-4-decanone, 6,6,7,7-tetramethyl-3-decanone, 6,6,7,7-tetramethyl-2-decanone, 5-ethyl-5-n-propyl-2-decanone, 5-ethyl-5-n-propyl-3-decanone, 5-ethyl-5-n-propyl-4-decanone, 6-ethyl-6-n-propyl-5-decanone, 6-ethyl-6-n-propyl-4-decanone, 6-ethyl-6-n-propyl-3-decanone, 6-ethyl-6-n-propyl-2-decanone, 3-n-butyl-3-n-propyl-2octanone, 4-butyl-4-ethyl-2-nonanone, 4-butyl-4-ethyl-3-nonanone, cyclopentanone, cyclohexanone, cycloheptanone, cyclooctanone, cyclododecanone, 2-methylcyclopentanone, 3-methylcyclopentanone, 2-methylcyclohexanone, 3-methylcyclohexanone, 4-methylcyclohexanone, 2-ethylcyclohexanone, 3-ethylcyclohexanone, 4-ethylcyclohexanone, cyclohexyl methyl ketone, 2-ethylcyclooctanone, 3-ethylcyclooctanone, 4-ethylcyclooctanone, 5-ethylcyclooctanone, cyclooctyl methyl ketone, 2,3-dimethylcyclohexanone, 3,4-dimethylcyclohexanone, 1-decalone, 2-decalone, norcamphor, 2-adamantanone, etc.

Examples of the benzene derivatives represented by the above formula (1) used as the starting material in the present invention include ethylbenzene, n-propylbenzene, n-butylbenzene, n-heptylbenzene, n-undecylbenzene, 2-chloroethylbenzene, 2-methoxyethylbenzene, 2-phenoxyethylbenzene, diphenylmethane, di(p-chlorophenyl)methane, di(p-tolyl)methane, di(p-methoxyphenyl)methane, di(m-phenoxyphenyl)methane, 1,2-diphenylethane, 1,3-diphenylpropane, o-ethyltoluene, m-ethyltoluene, p-ethyltoluene, o-chloroethylbenzene, m-chloroethylbenzene, p-chloroethylbenzene, p-bromoethylbenzene, p-methoxyethylbenzene, m-phenoxyethylbenzene, 2,4-dichloroethylbenzene, 2,4-dibromoethylbenzene, 2-chloro-4-methoxyethylbenzene, cumene, o-chlorocumene, m-chlorocumene, p-chlorocumene, p-bromocumene, p-methoxycumene, m-phenoxycumene, 2-phenylbutane, 2-phenylhexane, 3-phenylpentane, 3-phenylheptane, phenylcyclohexane, 1,3,5-triisopropylbenzene, etc.

The alcohols or the ketones which are the objective compounds of the present invention can be obtained, by use of the benzene derivatives mentioned above, as the alcohols represented by the above formula (3) or as the ketones represented by the above formula (5).

Examples of the alcohols represented by the formula (3) include 1-phenylethanol, 1-phenyl-1-propanol, 1-phenyl-1-butanol, 1-phenyl-1-heptanol, 1-phenyl-1-undecanol, 2-chloro-1-phenylethanol, 2-methoxy-1-phenylethanol, 2-phenoxy-1-phenylethanol, diphenylmethanol, di(p-chlorophenyl)methanol, di(p-tolyl)methanol, di(p-methoxyphenyl)methanol, di(m-phenoxyphenyl)methanol, 1,2-diphenylmethanol, 1,3-diphenyl-1-ethanol, 1-(o-tolyl)ethanol, 1-(m-tolyl)ethanol, 1-(p-tolyl)ethanol, 1-(2'-chlorophenyl)ethanol, 1-(3'-chlorophenyl)ethanol, 1-(4'-chlorophenyl)ethanol, 1-(4'-bromophenyl)ethanol, 1-(4'-methoxyphenyl)ethanol, 1-(3'-phenoxyphenyl)ethanol, 1-(2',4'-dichlorophenyl)ethanol, 1-(2',4'-dibromophenyl)ethanol, 1-(2'-chloro-4'-methyoxyphenyl)ethanol, 2-phenyl-2-propanol, 2-(2'-chlorophenyl)-2-propanol, 2-(3'-chlorophenyl)-2-propanol, 2-(4'-chlorophenyl)-2-propanol, 2-(4'-bromophenyl)-2-propanol, 2-(4'-methoxyphenyl)-2-propanol, 2-(3'-phenoxyphenyl)-2-propanol, 2-phenyl-2-butanol, 2-phenyl-2-hexanol, 3-phenyl-3-pentanol, 3-phenyl-3-heptanol, 1-phenylcyclohexanol, 2-(3',5'-diisopropylphenyl)-2-propanol, etc.

Examples of the ketones represented by the formula (5) include acetophenone, propiophenone, butanophenone, heptanophenone, undecaphenone, 2-chloroacetophenone, 2-methoxyacetophenone, 2-phenoxyacetophenone, benzophenone, 4,4'-dichlorobenzophenone, 4,4'-dimethylbenzophenone, 4,4'-dimethoxybenzophenone, 3,3'-diphenoxybenzophenone, 2-phenylacetophenone, 3-phenylpropiophenone, 2'-methylacetophenone, 3'-methylacetophenone, 4'-methylacetophenone, 2'-chloroacetophenone, 3'-chloroacetophenone, 4'-chloroacetophenone, 4'-bromoacetophenone, 4'-methoxyacetophenone, 3'-phenoxyacetophenone, 2',4'-dichloroacetophenone, 2',4'-dibromoacetophenone, 2'-chloro-4'-methoxyacetophenone, etc.

Examples of the benzene derivatives represented by the above formula (2) used as the starting material in the present invention include indan, tetralin, fluorene, 2,7-dibromofluorene, 2,7-dimethylfluorene, 2,7-dimethoxyfluorene, 2,7-diphenoxyfluorene, 1-methylindan, 9-methylfluorene, etc.

The alcohols or the ketones which are the objective compounds of the present invention can be obtained, by use of benzene derivatives mentioned above, as the alcohols represented by the above formula (4) or as the ketones represented by the above formula (6).

Examples of the alcohols represented by the formula (4) include 1-indanol, 1-tetralol, 9-fluorenol, 2,7-dibromo-9-fluorenol, 2,7-dimethyl-9-fluorenol, 2,7-dimethoxy-9-fluorenol, 2,7-diphenoxy-9-fluorenol, 1-methyl-1-indanol, 9-methyl-9-fluorenol, etc.

Examples of the ketones represented by the formula (6) include 1-indanone, 1-tetralone, fluorenone, 2,7-dibromofluorenone, 2,7-dimethylfluorenone, 2,7-dimethoxyfluorenone, 2,7-diphenoxyfluorenone, etc.

The transition metal catalyst may be a chromium-containing catalyst, manganese-containing catalyst, iron-containing catalyst, cobalt-containing catalyst, nickel-containing catalyst, copper-containing catalyst, ruthenium-containing catalyst, osmium-containing catalyst, and the like. Specific examples thereof include Cr, $CrCl_2.nH_2O$, $Cr_2(SO_4)_3.nH_2O$, $CrCl_3.nH_2O$, $CrF_3.nH_2O$, $Cr(OAc)_3 \cdot nH_2O$, $Cr(HCOO)_3.nH_2O$, $Cr(NO_3)_3.nH_2O$, $CrNH_4(SO_4)_2.nH_2O$, $CrPO_4.nH_2O$, $Cr_2O_3.nH_2O$, $CrO_3$, $Cr(acac)_3$, Mn, $MnCl_2.nH_2O$, $MnBr_2.nH_2O$, $MnF_2$, $MnSO_4.nH_2O$, $Mn(NO_3)_2.nH_2O$, $Mn(OAc)_2.nH_2O$, $Mn(ClO_4)_2.nH_2O$, $MnHPO_4.nH_2O$, $MnCO_3.nH_2O$, $Mn(OAc)_3.nH_2O$, $MnO_2$, $Mn(acac)_2.nH_2O$, $Mn(acac)_3.nH_2O$, Fe, $Fe(CO)_5$, $Fe(CO)_9$, $Fe(CO)_{12}$, $FeCl_2.nH_2O$, $FeBr_2.nH_2O$, $FeSO_4.nH_2O$, $Fe(ClO_4)_2.nH_2O$, $FeSO_4.(NH_4)_2SO_4.nH_2O$, $Fe_3(PO_4)_2.nH_2O$, $FeCl_3.nH_2O$, $FeF_3.nH_2O$, $Fe_2(SO_4)_3.nH_2O$, $Fe(NO_3)_3.nH_2O$, $Fe(OAc)_3$, $Fe(ClO_4)_3.nH_2O$, $FeNH_4(SO_4)_2.nH_2O$, $FePO_4.nH_2O$, $Fe_2O_3$, $Fe_3O_4$, $Fe(acac)_3$, Co, $CoCl_2.nH_2O$, $CoBr_2.nH_2O$, $CoI_2.nH_2O$, $CoF_2.nH_2O$, $CoSO_4.nH_2O$, $Co(NO_3)_2.nH_2O$, $Co(OAc)_2.nH_2O$, $CoSO_4.(NH_4)_2SO_4.nH_2O$, $Co_3(PO_4)_2.nH_2O$, $CoCO_3$, $Co(OH)_2$, $Co(acac)_2.nH_2O$, $Co(acac)_3.nH_2O$, $Co_3O_4$, Ni, $NiCl_2.nH_2O$, $NiBr_2.nH_2O$, $NiI_2.nH_2O$, $NiF_2.nH_2O$, $NiSO_4.nH_2O$, $Ni(NO_3)_2.nH_2O$, $Ni(OAc)_2.nH_2O$, $Ni(HCOO)_2.nH_2O$, $Ni(ClO_4)_2.nH_2O$, $NiSO_4.(NH_4)_2SO_4.nH_2O$, $NiCO_3$, $Ni(OH)_2$, $Ni(acac)_2.nH_2O$, NiO, $Ni_2O_3$, Cu, CuCl, CuBr, CuI, $CuCl_2.nH_2O$, $CuBr_2$, $CuF_2$, $CuSO_4.nH_2O$, $Cu(NO_3)_2.nH_2O$, $Cu(OAc)_2.nH_2O$, $Cu(ClO_4)_2.nH_2O$, $Cu(OH)_2$, $Cu(OCH_3)_2$, $Cu_3(PO_4)_2.nH_2O$, CuO, $Cu_2O$, $Cu(acac)_2$, Ru, $Ru_3(CO)_{12}$, $RuCl_2(PPh_3)_3$, $RuCl_3.nH_2O$, $RuO_2.nH_2O$, $RuO_4$, Os, $OsCl_3.nH_2O$ and $OsO_4$, wherein n is usually an integer of 0-12. Preferred among them are iron-containing catalysts and copper-containing catalysts, which cause little of environmental pollution.

These catalysts may also be used as a mixture thereof or after supported on heteropoly-acids, silica gel, carbon powders, pollers, etc. The amount of the catalyst to be used is not particularly limited, but is usually in the range of 0.01-200% by mole, preferably 0.1-5% by mole, relative to the alkane or the benzene derivative.

Specific examples of the aldehyde used in the present invention include formaldehyde, acetaldehyde, propionaldehyde, butanal, pentanal, hexanal, heptanal, decanal, 2-methylpropanal, cyclohexanecarboxaldehyde, isovaleraldehyde, pivalaldehyde, benzaldehyde, p-chlorobenzaldehyde, m-chlorobenzaldehyde, p-tolualdehyde, p-anisaldehyde, paraformaldehyde, paraldehyde, etc. Preferred among them are acetaldehyde, propionaldehyde, butanal and heptanal, which are easily available and have a low molecular weight. The amount of the aldehyde to be used is not critical but usually in the range of 0.1-1000% by mole, preferably 1-400% by mole, relative to the alkane or the benzene derivative.

The addition of the proton source is particularly effective when the transition metal catalyst is a simple substance or a heterogeneous catalyst.

Specific examples of the proton source include formic acid, acetic acid, monochloroacetic acid, dichloroacetic acid, trichloroacetic acid, monobromoacetic acid, trifluoroacetic acid, propanoic acid, butyric acid, heptanoic acid, decanoic acid, benzoic acid, p-toluenesulfonic acid, hydrochloric acid, hydrogen bromide, sulfuric acid, nitric acid, water, etc., preferred of which are acetic acid and benzoic acid.

Though the amount of the proton source to be used is not particularly restricted, it is usually in the range of 1-100 equivalents relative to the transition metal catalyst. The use of the proton source is not necessary when the transition metal catalyst contains water.

The reaction of the present invention may be conducted also in the presence of a solvent. As examples of solvents which may be used, mention may be made of halogenated hydrocarbons such as dichloromethane, chloroform, ethylene dichloride, etc., esters such as ethyl acetate, etc., nitriles such as acetonitrile, etc., and aromatic hydrocarbons such as benzene, toluene, xylene, monochlorobenzene, dichlorobenzene, etc.

The oxygen used in the present invention may be, besides oxygen, also air. The method of supplying the oxygen is not particularly limited, and the reaction is usually conducted while blowing oxygen or air into the reaction system or under an atmosphere of oxygen or air, either at normal pressure or under applied pressure ($<20$ atm for oxygen, $<100$ atm for air). The reaction temperature is usually in the range from 0° C. to the reflux temperature of the reaction mixture, preferably in the range from 20° C. to 80° C.

The reaction time is not particularly limited. The reaction mixture may be analyzed by suitable means such as gas chromatography (GC) and the point at which the rate of formation of the intended alcohol or ketone levels off may be taken as the end point of the reaction. The reaction time is usually in the range from 1 hour to 1 week. In the present reaction, the aldehyde used is converted into the corresponding carboxylic acid and hence can be easily separated from the intended product.

After completion of the reaction, the reaction mixture is washed with an aqueous sodium sulfite solution and aqueous sodium hydrogen carbonate solution, then concentrated and, if necessary and desired, subjected to additional operations such as rectification, whereby the intended alcohol or ketone can be obtained.

According to the process of the present invention, alcohols or ketones can be obtained under mild conditions and in one step from alkanes or alkylbenzene derivatives through the reaction thereof with oxygen by using an easily available transition metal catalyst and an aldehyde in the presence or absence of a proton source, so that the process is valuable also from the industrial point of view.

The present invention will be described in more detail below with reference to Examples, but the invention is in no way limited thereto.

EXAMPLES 1-26

To a mixture of 272 mg of adamantane, 3% by mole (relative to adamantane) of a catalyst, 4 mg of acetic acid and 10 ml of dichloromethane was added dropwise a solution of 897 mg of cyclohexanecarboxaldehyde in 2 ml of dichloromethane under an oxygen atmosphere at 25° C. over a period of 2 hours, and the resulting mixture was stirred at that temperature for further 15 hours. The reaction mixture obtained was analyzed by GC to obtain the results shown in Table 1. The products formed were subjected to quantitative determination by means of GC-IS (internal standard) method and identification of structure by means of GC-MS (mass spectrometry).

obtain the results shown in Table 3. The products formed were subjected to quantitative determination by means of GC-IS method and identification of structure by means of GC-MS.

TABLE 1

| Example | Catalyst | Conv,$^a$ % | Yield,$^b$ % | | | |
|---|---|---|---|---|---|---|
| | | | 1-adamantanol | 2-adamantanol | 2-adamantanone | total |
| 1 | Cr | 22 | 15(68) | 0.6(3) | 0.8(4) | 16(74) |
| 2 | CrCl$_2$ | 17 | 11(63) | 0.7(4) | 1.2(7) | 13(74) |
| 3 | Mn | 23 | 16(68) | 1.8(8) | 1.2(5) | 18(81) |
| 4 | Fe | 25 | 18(70) | 1.3(5) | 1.1(4) | 20(79) |
| 5 | FeCl$_2$.4H$_2$O | 16 | 12(78) | 1.3(9) | 1.2(8) | 15(95) |
| 6 | FeBr$_2$.2H$_2$O | 14 | 10(75) | 0.6(5) | 1.3(10) | 12(90) |
| 7 | FeCl$_3$.6H$_2$O | 21 | 11(51) | 1.6(8) | 1.5(7) | 14(65) |
| 8 | Fe(OAc)$_3$ | 28 | 22(78) | 1.5(5) | 1.5(5) | 25(89) |
| 9 | FeSO$_4$.7H$_2$O | 8.1 | 6.1(75) | 0.4(5) | 0.2(3) | 6.7(83) |
| 10 | Fe$_2$O$_3$ | 10 | 7.6(77) | 0.6(6) | 0.4(4) | 8.6(87) |
| 11 | Fe(acac)$_3$ | 20 | 16(78) | 1.1(6) | 1.0(5) | 18(88) |
| 12 | Co | 18 | 14(77) | 1.8(10) | 0.9(5) | 17(92) |
| 13 | CoCl$_2$ | 46 | 7.0(15) | 0.5(1) | 0.4(1) | 7.9(17) |
| 14 | Co(acac)$_2$.2H$_2$O | 14 | 9.0(66) | 0.7(6) | 0.8(6) | 11(78) |
| 15 | Co(acac)$_3$ | 11 | 8.8(77) | 0.8(7) | 0.9(8) | 11(91) |
| 16 | Ni | 21 | 16(76) | 1.8(9) | 0.3(2) | 18(87) |
| 17 | NiCl$_2$ | 18 | 10(55) | 4.2(23) | 0.3(2) | 15(80) |
| 18 | Ni(acac)$_2$ | 17 | 15(84) | 1.2(7) | 0.7(4) | 17(95) |
| 19 | Cu | 25 | 21(82) | 1.2(5) | 0.1(1) | 22(88) |
| 20 | CuCl | 25 | 20(83) | 1.4(6) | 0.3(1) | 22(89) |
| 21 | CuCl$_2$ | 9.0 | 7.6(85) | 0.5(5) | 0.2(2) | 8.3(92) |
| 22 | Ru | 15 | 11(72) | 1.1(7) | 0.8(5) | 13(84) |
| 23 | RuCl$_2$(PPh$_3$)$_3$ | 11 | 8.3(76) | 0.6(5) | 0.6(6) | 9.5(86) |
| 24 | RuCl$_3$.3H$_2$O | 23 | 18(77) | 0.9(4) | 1.0(5) | 19(85) |
| 25 | RuO$_2$ | 15 | 8.7(59) | 0.6(4) | 0.3(2) | 10(65) |
| 26 | Os | 9.2 | 7.5(82) | 0.5(6) | 0.3(4) | 8.3(91) |

$^a$Based on the starting adamantane.
$^b$Based on the starting adamantane. Values in parentheses correspond to yields based on the converted adamantane.

EXAMPLES 27–36

A mixture of 272 mg of adamantane, 3% by mole (relative to adamantane) of a catalyst, 264 mg of acetaldehyde and 12 ml of dichloromethane was stirred under an oxygen atmosphere at 25° C. for 17 hours. The reaction mixture was analyzed by GC to obtain the results shown in Table 2.

TABLE 2

| Example | Catalyst | Conv,$^a$ % | Yield,$^b$ % | | | |
|---|---|---|---|---|---|---|
| | | | 1-adamantanol | 2-adamantanol | 2-adamantanone | total |
| 27 | Cu | 27 | 22(80) | 1.1(4) | 0.4(2) | 23(86) |
| 28 | CuCl | 20 | 16(81) | 0.9(5) | 0.3(2) | 17(87) |
| 29 | Cu$_2$O | 26 | 22(85) | 0.9(4) | 0.0 | 23(89) |
| 30 | CuCl$_2$ | 4.0 | 4.0(99) | 0.0 | 0.0 | 4.0(99) |
| 31 | Cu(OAc)$_2$ | 26 | 21(83) | 1.0(4) | 0.0 | 22(87) |
| 32 | Cu(HCOO)$_2$ | 19 | 16(85) | 0.8(4) | 0.4(2) | 18(91) |
| 33 | Cu(OH)$_2$ | 29 | 25(87) | 1.5(5) | 0.9(3) | 28(95) |
| 34 | Cu(OCH$_3$)$_2$ | 32 | 24(75) | 1.3(4) | 1.1(4) | 26(83) |
| 35 | CuO | 10 | 9.9(99) | 0.0 | 0.0 | 9.9(99) |
| 36 | Cu(acac)$_2$ | 26 | 21(81) | 0.9(3) | 0.0 | 23(86) |

$^a$Based on the starting adamantane.
$^b$Based on the starting adamantane. Values in parentheses correspond to yields based on the converted adamantane.

EXAMPLES 37–67

A solution of 897 mg of cyclohexanecarboxaldehyde in 2 ml of dichloromethane was added dropwise to a mixture of 212 mg of ethylbenzene, 1% by mole (relative to ethylbenzene) of a catalyst, 1.2 mg of acetic acid and 10 ml of dichloromethane under an oxygen atmosphere at 25° C. over a period of 2 hours, and the mixture was stirred at that temperature for further 15 hours. The resulting reaction mixture was analyzed by GC to

TABLE 3

| Example | Catalyst | Conv,$^a$ % | Yield of acetophenone,$^b$ % |
|---|---|---|---|
| 37 | CrCl$_2$ | 10 | 6.5(64) |
| 38 | CrCl$_3$.6H$_2$O | 12 | 8.8(73) |
| 39 | Cr(OAc)$_3$.H$_2$O | 14 | 11(78) |
| 40 | Cr(acac)$_3$ | 12 | 9.1(76) |
| 41 | MnCl$_2$.4H$_2$O | 15 | 11(73) |
| 42 | Mn(OAc)$_2$.4H$_2$O | 14 | 10(71) |
| 43 | Mn(OAc)$_3$.nH$_2$O | 14 | 10(71) |
| 44 | Mn(acac)$_2$.4H$_2$O | 15 | 11(72) |
| 45 | Mn(acac)$_3$.2H$_2$O | 13 | 11(85) |
| 46 | Fe | 15 | 10(67) |
| 47 | FeCl$_2$.4H$_2$O | 10 | 7.5(78) |
| 48 | FeBr$_2$.2H$_2$O | 8.4 | 6.0(71) |
| 49 | FeCl$_3$.6H$_2$O | 13 | 7.0(56) |
| 50 | FeSO$_4$.7H$_2$O | 4.9 | 3.4(69) |
| 51 | Fe$_2$O$_3$ | 6.0 | 4.3(72) |
| 52 | Fe(acac)$_3$ | 12 | 9.0(75) |
| 53 | CoCl$_2$ | 28 | 4.0(14) |
| 54 | Co(OAc)$_2$.4H$_2$O | 14 | 10(71) |
| 55 | Co(acac)$_2$.2H$_2$O | 8.4 | 5.5(65) |
| 56 | Co(acac)$_3$ | 6.6 | 5.5(83) |
| 57 | NiCl$_2$ | 11 | 7.5(69) |

TABLE 3-continued

| Example | Catalyst | Conv,[a] % | Yield of acetophenone,[b] % |
|---|---|---|---|
| 58 | Ni(OAc)$_2$.4H$_2$O | 10 | 7.6(76) |
| 59 | Ni(acac)$_2$ | 10 | 8.5(83) |
| 60 | Cu | 16 | 13(80) |
| 61 | CuCl | 16 | 13(80) |
| 62 | Cu(OAc)$_2$ | 15 | 12(81) |
| 63 | RuCl$_2$(PPh$_3$)$_3$ | 6.6 | 4.8(73) |
| 64 | RuCl$_3$.3H$_2$O | 14 | 9.5(69) |
| 65 | RuO$_2$ | 9.0 | 5.0(56) |
| 66 | Os | 5.5 | 4.2(76) |
| 67 | OsCl$_3$.3H$_2$O | 4.3 | 3.9(91) |

[a]Based on the starting ethylbenzene.
[b]Based on the starting ethylbenzene. Values in parentheses correspond to yields based on the converted ethylbenzene.

EXAMPLES 68–71

To a mixture of 272 mg of adamantane, 3.4 mg of Fe, 4 mg of acetic acid and 10 ml of dichloromethane was added dropwise a solution of 4 equivalents (relative to adamantane) of an aldehyde in 2 ml of dichloromethane under an oxygen atmosphere at 25° C. over a period of 2 hours, and the mixture was stirred at that temperature for further 15 hours. The resulting reaction mixture was analyzed by GC to obtain the results shown in Table 4.

TABLE 4

| | | | Yield,[b] % | | | |
|---|---|---|---|---|---|---|
| Example | Aldehyde | Conv,[a] % | 1-adamantanol | 2-adamantanol | 2-adamantanone | total |
| 68 | acetaldehyde | 25 | 12(49) | 2.0(8) | 1.7(6) | 16(64) |
| 69 | haptanal | 33 | 25(75) | 1.9(6) | 1.6(5) | 28(86) |
| 70 | 2-methylpropanal | 34 | 25(73) | 1.6(5) | 1.9(6) | 28(84) |
| 71 | benzaldehyde | 25 | 17(68) | 0.9(4) | 0.5(2) | 18(73) |

[a]Based on the starting adamantane.
[b]Based on the starting adamantane. Values in parentheses correspond to yields based on the converted adamantane.

EXAMPLES 72–75

The same procedures as in Example 68 were followed except for using 16 mg of RuCl$_3$.3H$_2$O in place of 3.4 mg of Fe to obtain the results shown in Table 5.

TABLE 5

| | | | Yield,[b] % | | | |
|---|---|---|---|---|---|---|
| Example | Aldehyde | Conv,[a] % | 1-adamantanol | 2-adamantanol | 2-adamantanone | total |
| 72 | acetaldehyde | 32 | 21(64) | 0.5(1) | 1.1(3) | 22(68) |
| 73 | heptanal | 30 | 23(76) | 0.9(3) | 1.0(3) | 25(82) |
| 74 | decanal | 18 | 14(77) | 0.5(3) | 0.8(4) | 16(84) |
| 75 | 2-methylpropanal | 32 | 21(68) | 1.1(3) | 1.1(4) | 24(75) |

[a]Based on the starting adamantane.
[b]Based on the starting adamantane. Values in parentheses correspond to yields based on the converted adamantane.

EXAMPLES 76–80

A mixture of 272 mg of adamantane, 5.9 mg of Cu(OH)$_2$, 3 equivalents (relative to adamantane) of an aldehyde and 12 ml of dichloromethane was stirred under an oxygen atmosphere at 25° C. for 17 hours. The resulting reaction mixture was analyzed by GC to obtain the results shown in Table 6.

TABLE 6

| | | | Yield,[b] % | | | |
|---|---|---|---|---|---|---|
| Example | Aldehyde | Conv,[a] % | 1-adamantanol | 2-adamantanol | 2-adamantanone | total |
| 76 | butanal | 25 | 20(80) | 1.3(5) | 0.0 | 22(85) |
| 77 | 2-methylpropanal | 22 | 18(83) | 1.3(6) | 0.5(2) | 20(92) |
| 78 | cyclohexane-carboxaldehyde | 17 | 14(79) | 1.2(7) | 0.0 | 15(87) |
| 79 | pivalaldehyde | 13 | 11(90) | 1.0(8) | 0.3(2) | 13(100) |
| 80 | benzaldehyde | 29 | 21(74) | 1.9(7) | 0.0 | 23(81) |

[a]Based on the starting adamantane.
[b]Based on the starting adamantane. Values in parentheses correspond to yields based on the converted adamantane.

EXAMPLES 81–83

A solution of 914 mg of heptanal in 2 ml of a solvent was added dropwise to a mixture of 272 mg of adamantane, 16 mg of RuCl$_3$.3H$_2$O, 4 mg of acetic acid and 10 ml of the solvent under an oxygen atmosphere at 25° C. over a period of 2 hours, and the mixture was stirred at that temperature for further 15 hours. The resulting reaction mixture was analyzed by GC to obtain the results shown in Table 7.

TABLE 7

| | | | Yield,[b] % | | | |
|---|---|---|---|---|---|---|
| Example | Solvent | Conv,[a] % | 1-adamantanol | 2-adamantanol | 2-adamantanone | total |
| 81 | ethyl acetate | 18 | 14(81) | 1.4(8) | 1.6(9) | 17(98) |
| 82 | acetonitrile | 8.4 | 7.2(86) | 0.5(6) | 0.6(7) | 8.3(99) |
| 83 | benzene | 5.0 | 2.4(48) | 0.0 | 0.0 | 2.4(48) |

[a]Based on the starting adamantane.
[b]Based on the starting adamantane. Values in parentheses correspond to yields based on the converted adamantane.

EXAMPLES 84–87

A solution of heptanal in 2 ml of dichloromethane was added dropwise to a mixture of 272 mg of adamantane, 3.4 mg of Fe, 4 mg of acetic acid and 10 ml of dichloromethane under an oxygen atmosphere at 25° C.

analyzed by GC to obtain the results shown in Table 10.

TABLE 10

| Example | Equivalent each of heptanal (vs. adamantane) | Conv.,[a] % | Yield,[b] % | | | |
|---|---|---|---|---|---|---|
| | | | 1-adamantanol | 2-adamantanol | 2-adamantanone | total |
| 91 | 0.10 | 31 | 24(77) | 1.9(6) | 1.6(5) | 28(88) |
| 92 | 0.01 | 36 | 27(75) | 2.0(6) | 1.7(5) | 31(86) |

[a]Based on the starting adamantane.
[b]Based on the starting adamantane. Values in parentheses correspond to yields based on the converted adamantane.

over a period of 2 hours, and the mixture was stirred at that temperature for further 15 hours. The reaction mixture was analyzed by GC to obtain the results shown in Table 8.

TABLE 8

| Example | Equivalent of heptanal (vs. adamantane) | Conv.,[a] % | Yield,[b] % | | | |
|---|---|---|---|---|---|---|
| | | | 1-adamantanol | 2-adamantanol | 2-adamantanone | total |
| 84 | 1 | 19 | 13(71) | 1.2(6) | 2.0(5) | 17(82) |
| 85 | 2 | 30 | 22(76) | 1.6(5) | 1.6(5) | 26(86) |
| 86 | 3 | 32 | 24(74) | 2.0(6) | 1.6(5) | 28(86) |
| 87 | 5 | 31 | 21(67) | 1.7(5) | 1.4(5) | 24(77) |

[a]Based on the starting adamantane.
[b]Based on the starting adamantane. Values in parentheses correspond to yields based on the converted adamantane.

EXAMPLES 88–90

The same procedures as in Example 84 were followed except for using 16 mg of $RuCl_3 \cdot 3H_2O$ in place of 3.4 mg of Fe to obtain the results shown in Table 9.

TABLE 9

| Example | Equivalent of heptanal (vs. adamantane) | Conv.,[a] % | Yield,[b] % | | | |
|---|---|---|---|---|---|---|
| | | | 1-adamantanol | 2-adamantanol | 2-adamantanone | total |
| 88 | 2 | 23 | 18(78) | 0.9(4) | 0.9(4) | 20(86) |
| 89 | 3 | 35 | 27(78) | 1.1(3) | 1.2(4) | 29(85) |
| 90 | 5 | 28 | 20(72) | 0.7(2) | 0.8(3) | 22(77) |

[a]Based on the starting adamantane.
[b]Based on the starting adamantane. Values in parentheses correspond to yields based on the converted adamantane.

EXAMPLES 91–92

A solution of 914 mg of heptanal in 2 ml of dichloromethane was added dropwise to a mixture of 272 mg of adamantane, Fe, acetic acid and 10 ml of dichloromethane under an oxygen atmosphere at 25° C. over a period of 2 hours, and the mixture was stirred at that temperature for further 15 hours. The reaction mixture was analyzed by GC to obtain the results shown in Table 10.

EXAMPLES 93–94

The same procedures as in Example 91 were followed except for using $RuCl_3 \cdot 3H_2O$ in place of Fe and altering the amount of heptanal to 685 mg, to obtain the results shown in Table 11.

TABLE 11

| Example | Equivalent each of $RuCl_3 \cdot 3H_2O$ and acetic acid (vs. adamantane) | Conv.,[a] % | Yield,[b] % | | | |
|---|---|---|---|---|---|---|
| | | | 1-adamantanol | 2-adamantanol | 2-adamantanone | total |
| 93 | 0.10 | 35 | 26(75) | 1.7(5) | 1.9(5) | 30(85) |
| 94 | 0.01 | 28 | 19(71) | 0.9(3) | 1.0(4) | 21(78) |

[a]Based on the starting adamantane.
[b]Based on the starting adamantane. Values in parentheses correspond to yields based on the converted adamantane.

EXAMPLES 95–96

A solution of 914 mg of heptanal in 2 ml of dichloromethane was added dropwise to a mixture of 272 mg of adamantane, 1.1 mg of Fe, acetic acid and 10 ml of dichloromethane under an oxygen atmosphere at 25° C. over a period of 2 hours, and the mixture was stirred at that temperature for further 15 hours. The reaction mixture was analyzed by GC to obtain the results shown in Table 12.

TABLE 12

| Example | Equivalent of acetic acid (vs. Fe) | Conv.,[a] % | Yield,[b] % | | | |
|---|---|---|---|---|---|---|
| | | | 1-adamantanol | 2-adamantanol | 2-adamantanone | total |
| 95 | 100 | 26 | 21(79) | 1.5(6) | 1.3(5) | 23(90) |
| 96 | 10 | 36 | 26(72) | 1.9(5) | 1.7(5) | 29(82) |

[a]Based on the starting adamantane.
[b]Based on the starting adamantane. Values in parentheses correspond to yields based on the converted adamantane.

EXAMPLES 97-99

The same procedures as in Example 95 were followed except for using 16 mg of $RuCl_3.3H_2O$ in place of 1.1 mg of Fe and altering the amount of heptanal to 685 mg, to obtain the results shown in Table 13.

TABLE 13

| Example | Equivalent of acetic acid (vs. $RuCl_3.3H_2O$) | Conv,[a] % | Yield,[b] % 1-adamantanol | 2-adamantanol | 2-adamantanone | total |
|---|---|---|---|---|---|---|
| 97 | 100 | 29 | 20(68) | 1.3(4) | 1.4(5) | 23(78) |
| 98 | 10 | 34 | 22(63) | 1.3(4) | 1.4(4) | 24(71) |
| 99 | 0 | 31 | 22(70) | 1.3(4) | 1.5(5) | 25(79) |

[a]Based on the starting adamantane.
[b]Based on the starting adamantane. Values in parentheses correspond to yields based on the converted adamantane.

EXAMPLES 100-102

A solution of 914 mg of heptanal in 2 ml of dichloromethane was added dropwise to a mixture of 272 mg of adamantane, 1.1 mg of Fe, 1% by mole (relative to adamantane) of an acid and 10 ml of dichloromethane under an oxygen atmosphere at 25° C. over a period of 2 hours, and the mixture was stirred at that temperature for further 15 hours. The reaction mixture was analyzed by GC to obtain the results shown in Table 14.

TABLE 14

| Example | Acid | Conv,[a] % | Yield,[b] % 1-adamantanol | 2-adamantanol | 2-adamantanone | total |
|---|---|---|---|---|---|---|
| 100 | trifluoroacetic acid | 22 | 14(65) | 0.7(3) | 0.7(3) | 16(72) |
| 101 | decanoic acid | 7.0 | 5.4(78) | 0.3(4) | 0.2(3) | 5.9(85) |
| 102 | p-toluene-sulfonic acid monohydrate | 19 | 15(80) | 0.7(4) | 0.5(3) | 16(86) |

[a]Based on the starting adamantane.
[b]Based on the starting adamantane. Values in parentheses correspond to yields based on the converted adamantane.

EXAMPLES 103-106

A mixture of 272 mg of adamantane, 5.9 mg of Cu(OH)$_2$, 264 mg of acetaldehyde, 3% by mole (relative to adamantane) of an acid and 12 ml of dichloromethane was stirred under an oxygen atmosphere at 25° C. for 17 hours. The reaction mixture was analyzed by GC to obtain the results shown in Table 15.

TABLE 15

| Example | Acid | Conv,[a] % | Yield,[b] % 1-adamantanol | 2-adamantanol | 2-adamantanone | total |
|---|---|---|---|---|---|---|
| 103 | acetic acid | 25 | 23(90) | 0.9(4) | 0.0 | 24(93) |
| 104 | decanoic acid | 22 | 19(84) | 0.8(4) | 0.0 | 20(88) |
| 105 | benzoic acid | 28 | 23(85) | 1.1(4) | 0.0 | 25(89) |
| 106 | (water) | 20 | 16(80) | 0.8(4) | 0.2(1) | 17(84) |

[a]Based on the starting adamantane.
[b]Based on the starting adamantane. Values in parentheses correspond to yields based on the converted adamantane.

EXAMPLES 107-112

A solution of 914 mg of heptanal in 2 ml of dichloromethane was added dropwise to a mixture of 2 mmoles of an alkane, 1.1 mg of Fe, 1.2 mg of acetic acid and 10 ml of dichloromethane under an oxygen atmosphere at 25° C. over a period of 2 hours, and the mixture was stirred at that temperature for further 15 hours. The reaction mixture was analyzed by GC to obtain the results shown in Table 16. The products formed were subjected to quantitative determination by means of GC-IS method and identification of structure by means of GC-MS.

TABLE 16

| Example | Alkane | Conv,[a] % | Product | Yield,[b] % |
|---|---|---|---|---|
| 107 | n-heptane | 5.0 | heptanols[c] | 1.1(21) |
|  |  |  | heptanones[d] | 3.4(69) |
| 108 | n-decane | 4.8 | decanols[e] | 1.2(24) |
|  |  |  | decanones[f] | 3.0(63) |
| 109 | cyclohexane | 11 | cyclohexanol | 3.0(29) |
|  |  |  | cyclohexanone | 7.1(66) |
| 110 | cyclooctane | 15 | cyclooctanol | 1.8(12) |
|  |  |  | cyclooctanone | 12(76) |
| 111 | cyclododecane | 24 | cyclododecanol | 4.4(18) |
|  |  |  | cyclododecanone | 19(78) |
| 112 | methylcyclohexane | 16 | methylcyclohexanols[g] | 10(64) |
|  |  |  | methylcyclohexanones[h] | 3.1(20) |

[a]Based on the starting alkanes.
[b]Based on the starting alkanes. Values in parentheses correspond to yields based on the converted alkanes.
[c]2-ol:3-ol:4-ol = 46:36:18.
[d]2-one:3-one:4-one = 44:39:17.
[e]2-ol:3-ol:(4 + 5)-ols = 28:22:50.
[f]2-one:3-one:(4 + 5)-ones = 24:24:52.
[g]1-ol:2-ol:3-ol:4-ol = 69:6:18:7.
[h]2-one:3-one:4-one = 20:57:23.

EXAMPLES 113-117

The same procedures as in Examples 107-112 were followed except for using 16 mg of $RuCl_3.3H_2O$ in place of 1.1 mg of Fe and altering the amount of heptanal to 685 mg, to obtain the results shown in Table 17.

TABLE 17

| Example | Alkane | Conv,[a] % | Product | Yield,[b] % |
|---|---|---|---|---|
| 113 | n-heptane | 0.8 | heptanols | trace |
|  |  |  | heptanones[c] | 0.5(72) |
| 114 | n-decane | 2.0 | decanols[d] | 0.9(41) |
|  |  |  | decanones[e] | 0.9(44) |

TABLE 17-continued

| Example | Alkane | Conv,[a] % | Product | Yield,[b] % |
|---|---|---|---|---|
| 115 | cyclohexane | 3.1 | cyclohexanol | 1.1(36) |
|  |  |  | cyclohexanone | 1.6(53) |
| 116 | cyclooctane | 8.4 | cyclooctanol | 1.8(21) |
|  |  |  | cyclooctanone | 5.2(63) |
| 117 | methyl-cyclohexane | 11 | methylcyclo-hexanols[f] | 7.5(66) |
|  |  |  | methylcyclo-hexanones[g] | 2.6(23) |

[a]Based on the starting alkanes.
[b]Based on the starting alkanes. Values in parentheses correspond to yields based on the converted alkanes.
[c]2-one:3-one:4-one = 47:33:20.
[d]2-ol:3-ol:(4 + 5)-ols = 35:24:41.
[e]2-one:3-one:(4 + 5)-ones = 21:26:53.
[f]1-ol:2-ol:3-ol:4-ol = 87:3:7:3.
[g]2-one:3-one:4-one = 13:62:25.

EXAMPLES 118–122

A solution of 152 mg of heptanal in 2 ml of dichloromethane was added dropwise to a mixture of 13.3 mmoles of an alkane, 0.6 mg of Fe, 0.6 mg of acetic acid and 10 ml of dichloromethane under an oxygen atmosphere at 25° C. over a period of 2 hours, and the mixture was stirred at that temperature for further 15 hours. The reaction mixture was analyzed by GC to obtain the results shown in Table 18.

TABLE 18

| Example | Alkane | Conv,[a] % | Product | Yield,[b] % |
|---|---|---|---|---|
| 118 | n-heptane | 6.7 | heptanols[c] | 2.2(33) |
|  |  |  | heptanones[d] | 8.5(63) |
| 119 | n-decane | 6.5 | decanols[e] | 2.3(37) |
|  |  |  | decanones[f] | 8.0(61) |
| 120 | cyclohexane | 14 | cyclohexanol | 6.6(48) |
|  |  |  | cyclohexanone | 13(48) |
| 121 | cyclooctane | 17 | cyclooctanol | 6.0(36) |
|  |  |  | cyclooctanone | 20(59) |
| 122 | methyl-cyclohexane | 63 | methylcyclo-hexanols[g] | 46(73) |
|  |  |  | methylcyclo-hexanones[h] | 27(21) |

[a]Based on the starting heptanal.
[b]Based on the starting heptanal. Values in parentheses correspond to yields based on the converted alkanes.
[c]2-ol:3-ol:4-ol = 41:35:24.
[d]2-one:3-one:4-one = 44:38:18.
[e]2-ol:3-ol:(4 + 5)-ols = 30:22:48.
[f]2-one:3-one:(4 + 5)-ones = 24:21:55.
[g]1-ol:2-ol:3-ol:4-ol = 86:4:8:2.
[h]2-one:3-one:4-one = 17:63:20.

EXAMPLE 123

The same procedures as in Example 118 were followed except for using 2.6 mg of $RuCl_3 \cdot 3H_2O$ in place of 0.6 mg of Fe to obtain the following results.

Conversion: 70% (based on heptanal)

Methylcyclohexanols yield: 61% (based on heptanal), 88% (based on converted methylcyclohexane), 1-ol:2-ol: 3-ol:4-ol=91:2:5:2.

Methylcyclohexanones yield: 12% (based on heptanal), 8% (based on converted methylcyclohexane), 2-one:3-one:4-one=23:58:19.

EXAMPLES 124–128

A solution of 152 mg of heptanal in 2 ml of ethyl acetate was added to a mixture of 13.3 mmoles of an alkane, 2.6 mg of $RuCl_3 \cdot 3H_2O$, 0.6 mg of acetic acid and 10 ml of ethyl acetate under an oxygen atmosphere at 50° C., and the mixture was stirred at that temperature for 15 hours. The reaction mixture was analyzed by GC to obtain the results shown in Table 19.

TABLE 19

| Example | Alkane | Conv,[a] % | Product | Yield,[b] % |
|---|---|---|---|---|
| 124 | n-heptane | 3.8 | heptanols[c] | 0.9(30) |
|  |  |  | heptanones[d] | 5.1(68) |
| 125 | n-decane | 6.1 | decanols[e] | 1.4(24) |
|  |  |  | decanones[f] | 9.1(74) |
| 126 | cyclohexane | 6.6 | cyclohexanol | 2.4(35) |
|  |  |  | cyclohexanone | 8.1(61) |
| 127 | cyclooctane | 16 | cyclooctanol | 2.7(16) |
|  |  |  | cyclooctanone | 27(82) |
| 128 | methyl-cyclohexane | 78 | methylcyclo-hexanols[g] | 53(67) |
|  |  |  | methylcyclo-hexanones[h] | 45(29) |

[a]Based on the starting heptanal.
[b]Based on the starting heptanal. Values in parentheses correspond to yields based on the converted alkanes.
[c]2-ol:3-ol:4-ol = 40:40:20.
[d]2-one:3-one:4-one = 41:41:18.
[e]2-ol:3-ol:(4 + 5)-ols = 30:24:46.
[f]2-one:3-one:(4 + 5)-ones = 22:36:42.
[g]1-ol:2-ol:3-ol:4-ol = 96:1:2:1.
[h]2-one:3-one:4-one = 17:62:21.

EXAMPLES 129–134

A solution of 352 mg of acetaldehyde in 2 ml of dichloromethane was added dropwise to a mixture of 2 mmoles of an alkane, 1.1 mg of Fe, 1.2 mg of acetic acid and 10 ml of dichloromethane under an oxygen atmosphere at 25° C. over a period of 2 hours, and the mixture was stirred at that temperature for further 15 hours. The reaction mixture was analyzed by GC to obtain the results shown in Table 20.

TABLE 20

| Example | Alkane | Conv,[a] % | Product | Yield,[b] % |
|---|---|---|---|---|
| 129 | n-heptane | 5.8 | heptanols[c] | 1.0(17) |
|  |  |  | heptanones[d] | 4.8(82) |
| 130 | n-decane | 6.0 | decanols[e] | 0.5(9) |
|  |  |  | decanones[f] | 5.1(87) |
| 131 | cyclohexane | 8.0 | cyclohexanol | 2.6(33) |
|  |  |  | cyclohexanone | 5.0(62) |
| 132 | cyclooctane | 14 | cyclooctanol | 1.2(9) |
|  |  |  | cyclooctanone | 11(81) |
| 133 | methyl-cyclohexane | 11 | methylcyclo-hexanols[g] | 5.1(47) |
|  |  |  | methylcyclo-hexanones[h] | 4.7(42) |
| 134 | adamantane | 35 | adamantanol[i] | 27(77) |
|  |  |  | 2-adamanta-none | 2.7(8) |

[a]Based on the starting alkanes.
[b]Based on the starting alkanes. Values in parentheses correspond to yields based on the converted alkanes.
[c]2-ol:3-ol:4-ol = 40:40:20.
[d]2-one:3-one:4-one = 37:42:21.
[e]2-ol:3-ol:(4 + 5)-ols = 27:27:46.
[f]2-one:3-one:(4 + 5)-ones = 22:33:44.
[g]1-ol:2-ol:3-ol:4-ol = 64:7:22:7.
[h]2-one:3-one:4-one = 28:52:20.
[i]1-ol:2-ol = 92:8.

EXAMPLES 135–140

A mixture of 2 mmoles of an alkane, 5.9 mg of Cu-$(OH)_2$, 1.2 mg of acetic acid, 264 mg of acetaldehyde and 12 ml of dichloromethane was stirred under an oxygen atmosphere at 25° C. for 17 hours. The reaction mixture was analyzed by GC to obtain the results shown in Table 21.

TABLE 21

| Example | Alkane | Conv,[a] % | Product | Yield,[b] % |
|---|---|---|---|---|
| 135 | n-heptane | 3.2 | heptanols[c] | 0.5(16) |
|  |  |  | heptanones[d] | 2.7(84) |
| 136 | n-decane | 4.6 | decanols[e] | 0.7(15) |
|  |  |  | decanones[f] | 3.8(83) |

TABLE 21-continued

| Example | Alkane | Conv,[a] % | Product | Yield,[b] % |
|---|---|---|---|---|
| 137 | cyclohexane | 4.5 | cyclohexanol | 1.7(38) |
| | | | cyclohexanone | 2.6(58) |
| 138 | cyclooctane | 9.9 | cyclooctanol | 0.9(9) |
| | | | cyclooctanone | 8.7(88) |
| 139 | cyclo-dodecane | 12 | cyclo-dodecanol | 3.7(31) |
| | | | cyclo-dodecanone | 7.9(67) |
| 140 | methyl-cyclohexane | 8.6 | methylcyclo-hexanols[g] | 5.8(67) |
| | | | methylcyclo-hexanones[h] | 2.5(29) |

[a]Based on the starting alkanes.
[b]Based on the starting alkanes. Values in parentheses correspond to yields based on the converted alkanes.
[c]2-ol:3-ol:4-ol = 40:34:26.
[d]2-one:3-one:4-one = 40:43:17.
[e]2-ol:3-ol:(4 + 5)-ols = 20:20:60.
[f]2-one:3-one:(4 + 5)-ones = 27:27:46.
[g]1-ol:2-ol:3-ol:4-ol = 66:8:21:5.
[h]2-one:3-one:4-one = 18:61:21.

EXAMPLES 141–145

A solution of 914 mg of heptanal in 2 ml of dichloromethane was added dropwise to a mixture of 2 mmoles of a benzene derivative, 1.1 mg of Fe, 1.2 mg of acetic acid and 10 ml of dichloromethane under an oxygen atmosphere at 25° C. over a period of 2 hours, and the mixture was stirred at that temperature for further 15 hours. The reaction mixture was analyzed by GC to obtain the results shown in Table 22. The structure of the product formed was indentified by means of GC-MS.

TABLE 22

| Example | Substrate | Conv,[a] % | Product | Yield,[b] % |
|---|---|---|---|---|
| 141 | ethyl-benzene | 20 | 1-phenyl-ethanol | 3.3(16) |
| | | | acetophenone | 16(79) |
| 142 | indan | 31 | 1-indanol | 7.9(25) |
| | | | 1-indanone | 18(59) |
| 143 | p-ethyl-toluene | 49 | 1-(p-tolyl)-ethanol | 10(21) |
| | | | 4'-methyl-acetophenone | 26(54) |
| 144 | p-chloro-ethylbenzene | 15 | 1-(4'-chloro-phenyl)ethanol | 3.6(25) |
| | | | 1-(4'-chloro-phenyl)aceto-phenone | 11(73) |
| 145 | m-chloro-ethylbenzene | 8.8 | 1-(3'-chloro-phenyl)ethanol | 2.6(29) |
| | | | 1-(3'-chloro-phenyl)aceto-phenone | 6.2(71) |

[a]Based on the starting substrates.
[b]Based on the starting substrates. Values in parentheses correspond to yields based on the converted substrates.

EXAMPLES 146–147

The same procedures as in Example 141 or 142 were followed except for using 352 mg of acetaldehyde in place of 914 mg of heptanal to obtain the following results.

TABLE 23

| Example | Substrate | Conv,[a] % | Product | Yield,[b] % |
|---|---|---|---|---|
| 146 | ethyl-benzene | 26 | 1-phenyl-ethanol | 2.1(8) |
| | | | acetophenone | 14(56) |
| 147 | indan | 12 | 1-indanol | 2.1(18) |
| | | | 1-indanone | 6.3(54) |

[a]Based on the starting substrates.
[b]Based on the starting substrates. Values in parentheses correspond to yields based on the converted substrates.

EXAMPLE 148

A solution of 152 mg of heptanal in 2 ml of ethyl acetate was added dropwise to a mixture of 1.412 g of ethylbenzene, 2.6 mg of $RuCl_3.3H_2O$, 0.6 mg of acetic acid and 10 ml of ethyl acetate under an oxygen atmosphere at 50° C. over a period of 2 hours, and the mixture was stirred at that temperature for further 15 hours. The reaction mixture was analyzed by GC to obtain the following results.

Conversion: 48% (based on heptanal)
1-Phenylethanol yield: 15% (based on heptanal), 32% (based on converted ethylbenzene).
Acetophenone yield: 58% (based on heptanal), 61% (based on converted ethylbenzene).

EXAMPLE 149

A mixture of 20.2 g of cyclohexane, 3.4 mg of Fe, 3.6 mg of acetic acid and 1.055 g of paraldehyde was stirred under an oxygen atmosphere at 70° C. for 1 week. The reaction mixture was analyzed by GC to obtain the following results.

Cyclohexanol yield: 5.8% (based on paraldehyde), turnover number: 23
Cyclohexanone yield: 29.3% (based on paraldehyde), turnover number: 102

EXAMPLE 150

The same procedures as in Example 149 were followed except for using 2.741 g of heptanal in place of paraldehyde and altering the amount of acetic acid to 360 mg, to obtain the following results.

Cyclohexanol yield: 9.6% (based on heptanal), turnover number: 38
Cyclohexanone yield: 22.5% (based on heptanal), turnover number: 90

EXAMPLE 151

The same procedures as in Example 149 were followed except for using 1.057 g of acetaldehyde in place of paraldehyde and altering the amount of acetic acid to 360 mg, to obtain the following results.

Cyclohexanol yield: 3.4% (based on acetaldehyde) turnover number: 14
Cyclohexanone yield: 8.7% (based on acetaldehyde) turnover number: 35

EXAMPLE 152

A mixture of 67.3 g of cyclohexane, 11 mg of Fe, 12 mg of acetic acid and 3.52 g of acetaldehyde was placed in an autoclave and stirred under an applied oxygen pressure (8 kg/cm$^2$) at 70° C. for 24 hours. The reaction mixture was analyzed by GC to obtain the following results.

Cyclohexane conversion: 23.1% (based on acetaldehyde)
Cyclohexanol yield: 9.1% (based on acetaldehyde), 39.5% (based on converted cyclohexane) turnover number: 36

Cyclohexanone yield: 27.4% (based on acetaldehyde), 59.5% (based on converted cyclohexane) turnover number: 110

EXAMPLE 153

A mixture of 6.73 g of cyclohexane, 1.1 mg of Fe, 1.2 mg of acetic acid and 352 mg of acetaldehyde was placed in an autoclave and stirred under an applied air pressure (10 kg/cm$^2$) at 70° C. for 5 days. The reaction mixture was analyzed by GC to obtain the following results.

Cyclohexane conversion: 20.1% (based on acetaldehyde),

Cyclohexanol yield: 7.7% (based on acetaldehyde) 38.3% (based on converted cyclohexane) turnover number: 31

Cyclohexanone yield: 24.8% (based on acetaldehyde), 61.7% (based on converted cyclohexane) turnover number: 99

What is claimed is:

1. A process for producing a corresponding alcohol or ketone derived from the alkane defined below, or alcohol represented by the formula (3)

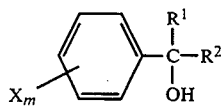  (3)

wherein R$^1$, R$^2$, X and m are as defined below or by the formula (4)

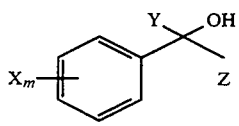  (4)

X, Y, Z and m are as defined below, or a ketone represented by the formula (5)

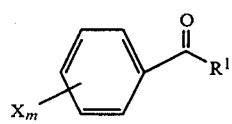  (5)

wherein R$^1$, X and m are as defined below, or by the formula (6)

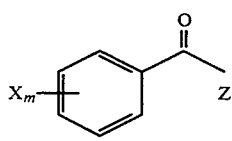  (6)

wherein X, Z and m are as defined below, which comprises reacting a straight-chain, a branched-chain, or a cyclic alkane of 1-20 carbon atoms or a benzene derivative represented by formula (1)

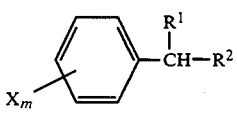  (1)

wherein R$^1$ and R$^2$ can be the same or different, and each denotes a hydrogen atom, a (C$_1$-C$_{20}$) alkyl group, an alkyl group substituted with a halogen, alkoxy or phenoxy, a phenyl group substituted or unsubstituted with a halogen, alkyl, alkoxy or phenoxy, or a phenyl alkyl group substituted or unsubstituted with a halogen, alkyl, alkoxy or phenoxy, where R$^1$ and R$^2$ conjointly as —CHR$^1$(R$^2$) in its entirety denote a (C$_3$-C$_{12}$) cycloalkyl group substituted or unsubstituted with a halogen or alkyl, alkoxy, phenyl or phenoxy; X can be the same or different, and denotes a hydrogen atom, a halogen atom, a (C$_1$-C$_6$) alkyl group, a (C$_1$-C$_6$) alkoxy group, a phenyl group or a phenoxy group; m denotes 1 or 2, or by formula (2)

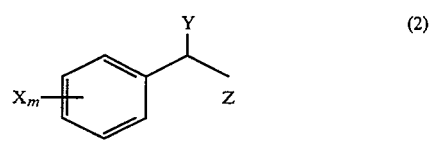  (2)

wherein Y denotes a hydrogen atom, a halogen atom, a (C$_1$-C$_6$) alkyl group, a (C$_1$-C$_6$) alkyl group, a (C$_1$-C$_6$) alkoxy group, a phenyl group or a phenoxy group; Z denotes a group of —CH$_2$CH$_2$—, —CH$_2$CH$_2$CH$_2$— or

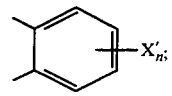

X and X' can be the same or different, and each denotes a hydrogen atom, a halogen atom, a (C$_1$-C$_6$) alkyl group, a (C$_1$-C$_6$) alkoxy group, a phenyl group, or a phenoxy group; and m and n each independently denote 1 or 2, with oxygen in the absence or presence of a proton source and in the presence of a transition metal catalyst and an aldehyde wherein the transition metal catalyst is present in an amount of 0.01–200% percent by mole relative to the alkane or benzene derivative and wherein the reaction temperature is in the range of from 20° C. to 80° C.

2. The process according to claim 1 wherein the transition metal catalyst is a chromium-containing catalyst, manganese-containing catalyst, iron-containing catalyst, cobalt-containing catalyst, nickel-containing catalyst, copper-containing catalyst, ruthenium-containing catalyst or osmium-containing catalyst.

3. The process according to claim 2 wherein the chromium-containing catalyst is Cr, CrCl$_2$.nH$_2$O, CrCl$_3$.nH$_2$O, Cr(OAc)$_3$.nH$_2$O or Cr(acac)$_3$.

4. The process according to claim 2 wherein the manganese-containing catalyst is Mn, MnCl$_2$.nH$_2$O, Mn(OAc)$_2$.nH$_2$O, Mn(OAc)$_3$.nH$_2$O, Mn(acac)$_2$.nH$_2$O or Mn(acac)$_3$.nH$_2$O.

5. The process according to claim 2 wherein the iron-containing catalyst is Fe, FeCl$_2$.nH$_2$O, FeCl$_3$.nH$_2$O, Fe(OAc)$_3$ or Fe(acac)$_3$.

6. The process according to claim 2 wherein the cobalt-containing catalyst is Co, CoCl$_2$.nH$_2$O, Co(OAc)$_2$.nH$_2$O, Co(acac)$_2$.nH$_2$O or Co(acac)$_3$.nH$_2$O.

7. The process according to claim 2 wherein the nickel-containing catalyst is Ni, NiCl$_2$.nH$_2$O, Ni(OAc)$_2$.nH$_2$O or Ni(acac)$_2$.nH$_2$O.

8. The process according to claim 2 wherein the copper-containing catalyst is Cu, CuCl, Cu(OAc)$_2$.nH$_2$O, Cu(OH)$_2$, Cu(OCH$_3$)$_2$, Cu$_2$O or Cu(acac)$_2$.

9. The process according to claim 2 wherein the ruthenium-containing catalyst is Ru, RuCl$_3$.nH$_2$O or RuO$_2$.

10. The process according to claim 2 wherein the osmium-containing catalyst is Os or OsCl$_3$.nH$_2$O.

11. The process according to claim 1 wherein the aldehyde is formaldehyde, acetaldehyde, propionaldehyde, butanal, pentanal, hexanal, heptanal, decanal, 2-methylpropanal, cyclohexanecarboxaldehyde, isovaleraldehyde, pivalaldehyde, benzaldehyde, p-chlorobenzaldehyde, m-chlorobenzaldehyde, p-tolualdehyde, p-anisaldehyde, paraformaldehyde or paraldehyde.

12. The process according to claim 1 wherein the proton source is formic acid, acetic acid, monochloroacetic acid, dichloroacetic acid, trichloroacetic acid, monobromoacetic acid, trifluoroacetic acid, propanoic acid, butyric acid, heptanoic acid, decanoic acid, benzoic acid, p-toluenesulfonic acid, hydrochloric acid, hydrogen bromide, sulfuric acid, nitric acid or water.

13. The process according to claim 1 wherein the aldehyde is used in an amount of 0.1–1000% by mole relative to the alkane or the benzene derivative.

14. The process according to claim 1 wherein the proton source is used in an amount of 1–100 equivalents relative to the transition metal catalyst.

15. The process according to claim 1 wherein the reaction time is 1 hour to 1 week.

16. The process according to claim 1 wherein the reaction is conducted without a solvent.

17. The process according to claim 15, wherein the catalyst is present in an amount of 0.1–5% by mole relative to the alkane or the benzene derivative.

* * * * *